(12) United States Patent
Forward

(10) Patent No.: US 8,897,877 B2
(45) Date of Patent: Nov. 25, 2014

(54) METHOD AND DEVICE FOR INCREASING TESTOSTERONE PRODUCTION IN A MALE

(76) Inventor: Robert D. Forward, Chatsworth, CA (US)

(*) Notice: Subject to any disclaimer, the term of this patent is extended or adjusted under 35 U.S.C. 154(b) by 323 days.

(21) Appl. No.: 13/310,852

(22) Filed: Dec. 5, 2011

(65) Prior Publication Data

US 2013/0144357 A1    Jun. 6, 2013

(51) Int. Cl.
*A61N 1/36* (2006.01)

(52) U.S. Cl.
USPC ............................................ 607/39

(58) Field of Classification Search
USPC ............................................ 607/39
See application file for complete search history.

(56) References Cited

U.S. PATENT DOCUMENTS

| | | |
|---|---|---|
| 6,553,266 B1 | 4/2003 | Yuang |
| RE41,463 E | 7/2010 | Boutos |
| 2005/0055067 A1* | 3/2005 | Yu .................................. 607/48 |

OTHER PUBLICATIONS

Zhu, B., et al, Effect of Stimulation of the Superior and Inferior Spermatic Nerves on Testosterone Secrection and Testicular Blood Flow, English Abstract of Chinese Article, found on PubMed on Aug. 29, 2011 (1 page).

* cited by examiner

*Primary Examiner* — Alyssa M Alter
(74) *Attorney, Agent, or Firm* — Wood Herron & Evans, LLP

(57) ABSTRACT

Described herein is a device and method for stimulating testosterone production in a subject. The device includes a first electrode, a second electrode, and a power source. The first electrode is configured to contact the skin in the pubic region of the subject and is electrically coupled to the power source. The second electrode is configured to contact the skin on the scrotum of the subject and is also electrically coupled to the power source. The power source is configured to deliver about 6 volts or less to the first or second electrodes. The device may further include a snug fitting undergarment for maintaining contact between the first and second electrodes and the subject's skin. The method is directed to the application of a low voltage to the testicles of a subject to stimulate the production of testosterone.

7 Claims, 1 Drawing Sheet

METHOD AND DEVICE FOR INCREASING TESTOSTERONE PRODUCTION IN A MALE

FIELD

The present invention is directed to methods and devices for stimulating the production of testosterone in a subject, and more particularly to methods and devices for stimulating the production of testosterone in a subject by applying a voltage to the subject's gonads.

BACKGROUND

Testosterone is one of the hormones in men that spur the development of secondary sexual characteristics. Testosterone is produced by the testes in response to certain hormonal and nervous system stimulation. Testosterone production typically peaks in the late teens and early twenties and gradually declines with age. It has been estimated that one third of men over the age of 45 years of age have low testosterone levels.

Normally, a male's total testosterone blood level is in the range of about 270 ng/dL to about 1070 ng/dL (about 9 nmol/L to about 38 nmol/L), with free testosterone blood levels falling in the range of about 50 pg/mL to about 210 pg/mL (about 174 pmol/L to about 729 pmol/L). Levels below these ranges indicate clinically low testosterone levels. Individuals having lower testosterone levels, but not low enough to result in a clinical diagnosis of a low testosterone level may also suffer from symptoms associated with the lower level.

The symptoms of low testosterone levels in males include decreased libido, erectile dysfunction, loss of body and/or facial hair, weakened bones, increased body fat, and fatigue. Currently, subjects with symptoms of low testosterone levels are treated with hormone replacement therapy such as Androgel® and Testim®. Testosterone replacements are typically applied transdermally or transmucosally and can have a number of side effects including rash, itching, or irritation at the site where the testosterone is applied. There is also the potential for benign prostatic hypertrophy, prostate cancer, sleep apnea, erythrocytosis, and congestive heart failure with these hormone replacement therapies. Methods of safely increasing the endogenous production of testosterone are needed that may avoid some or all of the potential side effects of testosterone hormone replacement therapies.

SUMMARY

Described herein are devices and methods for increasing the endogenous production of testosterone in a subject. The devices include a first electrode, a second electrode, and a power source. The first electrode is configured to contact the skin in the pubic region of the subject and is electrically coupled to the power source by a first wire. The second electrode is configured to contact the skin on the scrotum of the subject and is electrically coupled to the power source by a second wire. The power source is configured to deliver about 6 volts or less to one of the first electrode and the second electrode. The devices may also include an undergarment configured to maintain the first and second electrodes in contact with the skin in the desired area of the subject's body, namely, the pubic region and the scrotum.

The methods include contacting the skin of the subject's pubic region with a first electrode and contacting the skin of the subject's scrotum with a second electrode. A voltage from a power source is supplied to one of the first electrode or the second electrode such that at least a portion of the voltage passes through the skin of the subject from one electrode to the other electrode. The voltage supplied is about 6 volts or less and is sufficient to stimulate testosterone production in the subject.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the embodiments of the invention.

DETAILED DESCRIPTION

Figure 1A:
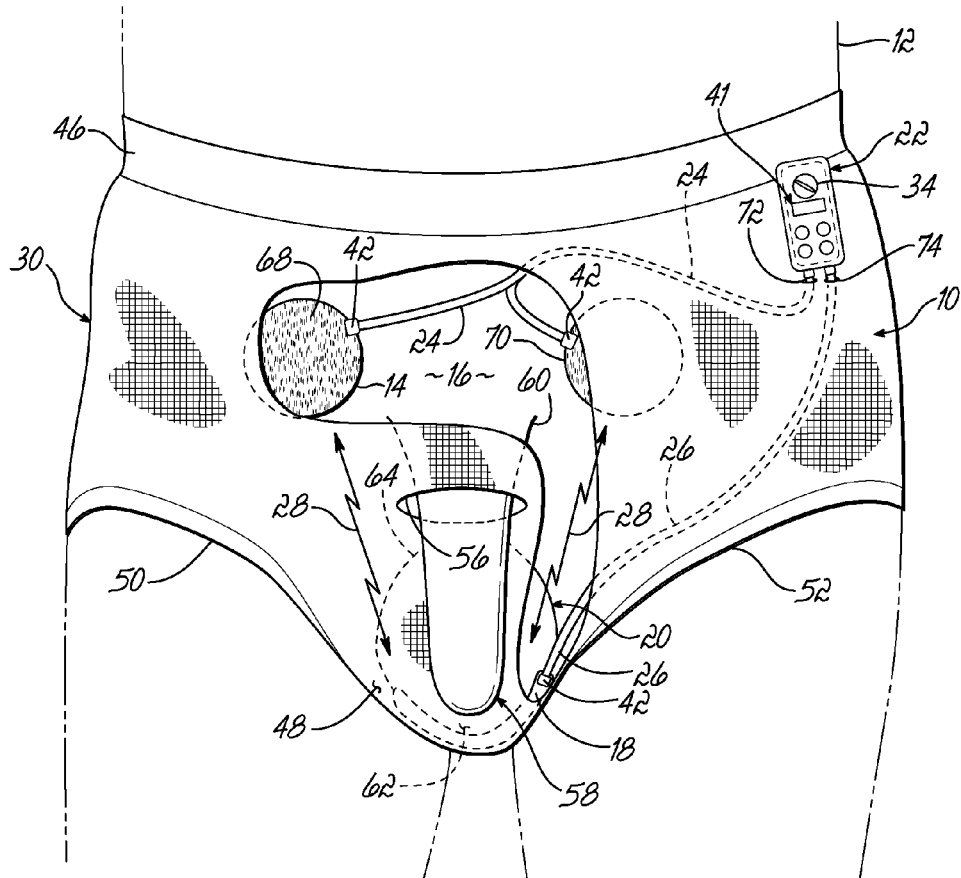
FIG. 1A is a diagrammatic front partial cut-away view showing an embodiment of the invention.

With reference to FIG. 1A, embodiments of the present invention are directed to a device 10 for stimulating the endogenous production of testosterone in a male subject 12. The device 10 generally includes a first electrode 14 configured to contact the skin in the pubic region 16 of a subject 12 and a second electrode 18 configure to contact the skin of the scrotum 20 of the subject 12. The first and second electrodes 14, 18 are coupled to a power source 22, such as by a first electrically conducting wire 24 extending between the first electrode 14 and the power source 22, and a second electrically conducting wire 26 extending between the second electrode 18 and the power source 22. The power source 22 supplies voltage 28 to one of the first electrode 14 or the second electrode 18 such that at least some of the voltage 28 passes through the subject 12 to the other of the first or second electrodes 14, 18. In some embodiments, the device 10 may optionally further include an undergarment 30 configured to maintain the first electrode 14 in a position to contact the skin in the pubic region 16 of the subject 12 and to maintain the second electrode 18 in a position to contact the skin on the scrotum 20 of the subject 12.

In one embodiment, the first electrode 14 delivers the voltage 28 from the power source 22 to the skin of the subject 12 and the second electrode 18 closes the circuit between the skin and the power source 22. In another embodiment, the second electrode 18 delivers the voltage 28 from the power source 22 to the skin of the subject 12 and the first electrode 14 closes the circuit between the skin and the power source 22. In some embodiments, the voltage 28 can be delivered to either of the first or second electrodes 14, 18, as desired such as with a manual switching circuit, an automatically switching circuit, by plugging the wires 24, 26 from the first and second electrodes 14, 18 into their respective opposite polarity contact points on the power source 22, or by moving the electrodes 14, 18 to contact the skin of the other desired location (i.e., moving an electrode that had been contacting the skin in the pubic region 16 to contact the skin on the scrotum 20 and vice versa).

The device 10 may further include additional circuitry for controlling the voltage supply by the power source 22 to the first or second electrodes 14, 18. In one embodiment, the device 10 includes an on/off switch 34 configured to interrupt the voltage between the power source 22 and the first or second electrodes 14, 18 as shown in FIG. 1B.

Figure 1B:
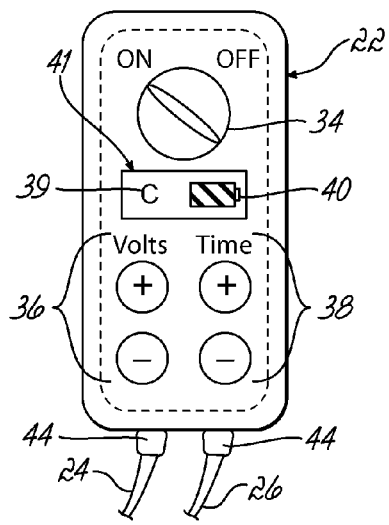
FIG. 1B is a close up front view of a power source with operating controls in accordance with embodiments of the invention.

The device 10 may also optionally include voltage adjusting component 36 for adjusting the voltage 28 from the power source 22 to the first or second electrodes 14, 18 (FIG. 1B). The voltage adjusting component 36 allows for the voltage 28 to be adjusted from about 6 volts or less or between about 1.5 volts and about 6 volts. Voltage adjusting components are generally known to those of skill in the art with exemplary voltage adjusting components including a rheostat, a potentiometer, a resistor switch, a digital resistor control circuit, thermostat, and combinations thereof. The voltage adjusting component 36 may be manually controlled by the user or automatically controlled such as by a computer code or a circuit. The voltage adjusting component 36 may allow the user to select a desired voltage 28 to be delivered to the electrodes 14, 18. In addition, the voltage adjusting component 36 may allow for the voltage 28 to cycle between a higher voltage and a lower voltage, such as by following a programmed routine which could be included in the circuitry of the voltage adjusting component 36 or in a separate circuit in either a hard wired or programmable format running a computer code.

The device 10 may also optionally include a timer 38 for controlling the duration that the voltage 28 from the power source 22 is supplied to the first or second electrodes 14, 18. The timer 38 may be manually set by the subject or automatically controlled such as by a computer code or a circuit. The timer 38 may control the total duration that voltage 28 is supplied to the subject 12 such as in a range between about 2 hours and about 12 hours, or in a range between about 4 hours and about 10 hours, or in a range between about 6 hours and about 8 hours, or any time point between any of these ranges. The timer 38 may also allow the voltage 28 to be supplied in pulses wherein for each pulse the voltage 28 is supplied for a period of time that alternates with a period of time during which no voltage is supplied.

The device may optionally include additional indicators of function, such as a continuity indicator, a battery charge level indicator, and combinations thereof. An exemplary continuity indicator could be a low voltage LED bulb or a notation on a low voltage LCD display 39 that indicates continuity between the electrodes. Likewise, an exemplary battery charge level indicator could also be a low voltage LED bulb or a notation on a low voltage LCD display 40 that indicates the charge level of the battery. In one embodiment, the exemplary LED bulb can change colors to indicate the level of charge in the battery. Both the continuity indicator and the battery charge indicator could be included in a single display, such as a low voltage LCD display 41.

The first and second electrodes 14, 18 each include a contact 42 for electrically coupling the first and second electrodes 14, 18 to the respective first and second electrically conducting wires 24, 26. The contact 42 may be fixed such that the wire 24, 26 and the electrode 14, 18 are permanently joined such as by soldering, or temporary such that the electrode 14, 18 and wire 24, 26 can be easily uncoupled from one another. Exemplary temporary contacts include mating male and female snap connectors, wherein the electrode includes one of a male or female snap connector, and the wire includes the other mating male or female connector. Temporary contacts allow for the easy and independent replacement of electrodes and wires. Similar permanent and temporary contacts 44 may be used to couple the first and second wires 24, 26 to the power source 22.

The surfaces of the first and second electrodes 14, 18 that are in contact with the skin, i.e., the skin contacts, may be made of materials routinely used in the art to deliver voltage to the skin of a subject. Advantageously, the skin contacts are made of materials that are well tolerated by the skin and that will not ionize during use. The skin contacts are made of materials that allow for the even distribution of voltage 28 to the skin so as to prevent "hot spots" that could burn the skin of the subject 12. Suitable exemplary electrodes presently available are those used with TENS devices. The skin contacts can be made of a number of materials, such as carbon graphite electrodes (such as are available from Tyco Gel or Austin Medical), electrically conducting rubber sheets, conductive foam rubber, and combinations thereof. The electrodes may be used with or without the additional use of a conductive gel such as Parker-Spectra 360 or conductive aloe gel.

The skin contacts of the electrodes 14, 18 are typically of a size sufficient to prevent the formation of "hot spots" or burned areas of skin during the application of voltage 28. Preferably, the electrodes 14, 18 have a greatest first dimension in the range between about 1 inch to about 3 inches and a greatest second dimension perpendicular to the first dimension in the range between about 1 inch to about 3 inches. More preferably, the first and second dimensions are about 1.75 inches. The electrodes can be any convenient shape such as generally round (e.g., circular or elliptical), generally quadrilateral (e.g. square, rectangular, trapezoidal, rhomboidal), generally triangular, or any suitable shape.

The electrodes 14, 18 are temporarily maintained in contact with the desired location on the skin. In one embodiment, the electrodes may have an adhesive to temporarily adhere the skin contact of the electrode 14, 18 to the skin of the subject 12. Preferably, contact between the skin contact of the electrode 14, 18 and the skin of the subject is maintained with a snug fitting undergarment 30 such that no adhesive is needed on the electrode. An exemplary undergarment includes a waistband portion 46, a pouch portion 48, a first leg opening 50, and a second leg opening 52. The first leg opening 50 is separated from the second leg opening 52 by the pouch portion 48. The pouch portion 48 and the waistband portion 46 may be formed from an integral piece of material or may be formed from separate sections of material that are coupled together such as by stitching. The first and second leg openings 50, 52 may be further defined by a seat or one or two bands that extends between a portion of the pouch 48 and the waistband 46. For example, in one embodiment, the undergarment 30 is similar to a snug fitting pair of briefs. In another embodiment, the undergarment is similar to an athletic supporter (e.g., a jockstrap). In a further embodiment, the undergarment is similar to a thong. Other snug fitting types of undergarments can be used so long as the undergarment is capable of maintaining contact between the first and second electrodes 14, 18 with the skin in the desired locations. The waistband portion 46 or the pouch portion 48 (or a combination thereof) may maintain the first electrode 14 in contact with the skin of the pubic region 16. The pouch portion 48 generally maintains the second electrode 18 in contact with the skin of the scrotum 20.

In some embodiments, the front of the undergarment 30, i.e., the pouch portion 48, includes an opening 56 through which the penis 58 may pass. This opening 56 provides the advantage that should be subject's 12 penis 58 become erect during use of the device, the erection will not push the undergarment 30 away from the skin thereby causing a loss of contact between one or both of the first and second electrodes 14, 18.

The first electrode 14 is positioned to contact the skin in the pubic region 16 generally along the edge of the pubic hair of a subject 12 typically grows (not shown). The first electrode 14 may be positioned on the skin in the region directly above distal end 60 of the penis 58 and may be offset mediolaterally by about one inch to about three inches. It may be necessary to remove the pubic hair from the pubic area 16 for the first electrode 14. The position of the first electrode 14 may maintained with an adhesive or by an undergarment such as the pouch portion 48 or the waistband portion 46 of the undergarment 30.

The second electrode 18 is positioned to contact the skin of the scrotum 20 of the subject 12. The second electrode 18 may be positioned on the skin near a proximal end 62 of the scrotum 20 or midway down the length of the scrotum 20, wherein the length of the scrotum 20 is determined by the axis that runs between the proximal end 62 of the scrotum 20 and the distal end 64 of the scrotum 20. It may be necessary to remove the pubic hair from the area for the second electrode 18. The position of the second electrode 18 may be maintained with either an adhesive or an undergarment 30, such as the pouch portion 48 of the undergarment 30.

When the device 10 is used with an undergarment 30, the relative positions of the first and/or second electrodes 14, 18 on the undergarment may be maintained on the undergarment with a coupling mechanism that couples the first and/or second electrode 14, 18 to the undergarment 30 in the area overlying the desired area of skin, i.e., over the pubic region 16 for the first electrode 14 and the scrotum 20 for the second electrode 18. The electrodes may be made into the undergarment or temporarily attached. Exemplary coupling mechanisms include a latch hook fastener, a magnet, a snap, an adhesive, a stitching, a button, a pocket, and combinations thereof. The coupling mechanism typically includes a component located on the back of the electrode, i.e., the side opposite the skin contact, and has a corresponding component located in the undergarment that, when worn by the subject, would overlay the desired area of skin. For example, as shown in FIG. 1A, the back side of the electrode 14, 18 may have a latch fastener 68 and the undergarment 30 may have a corresponding hook fastener (or vice versa).

The undergarment may likewise include an attachment structure for holding the power source. The attachment structure can include a pocket, a latch/hook structure, a snap, etc. Likewise, the undergarment 30 may also include openings 72, 74 to allow the first and second wires 24, 26 to pass through.

The skin contacts of the first and second electrodes 14, 18 may optionally be coated with conductive gel. The conductive gel is placed between the skin contact and the skin. While the conductive gel is between the skin contact and the skin, an electrode used with such a conductive gel is still considered to be in contact with the skin of the subject. Similarly, in embodiments having an adhesive on the skin contact to maintain the desired position of the electrode are also considered to be in contact with the skin despite the presence of an adhesive layer on the skin contact surface.

Aspects of the invention are directed to methods of stimulating testosterone production in a male subject 12 with electrical stimulation of the testicles such as with the devices described herein. The method includes contacting the skin in the pubic region 16 of the subject 12 with a first electrode 14 and contacting the skin of the scrotum 20 of the subject 12 with a second electrode 18. One of the first or second electrodes 14, 18 is then supplied with a voltage 28 from a power source 22. The voltage 28 passes between the first electrode 14 and the second electrode 18 through the skin of the subject 12 to stimulate the endogenous production of testosterone. The voltage 28 is supplied at level that is tolerable to the subject 12 without causing discomfort or burns when the voltage 28 is supplied for a desired duration. Typically, the voltage supplied is less than about 6 volts, or less than about 4.5 volts, or in a range between about 1.5 volts and about 6 volts. Preferably the voltage supplied is in the range from about 1.5 volts to about 4.5 volts or about 3 volts. While the present description references voltage, one of ordinary skill in the art will appreciate that a corresponding amperage may also be used, i.e., between about 0.001 amps to about 0.003 amps.

The voltage 28 is supplied to a subject for specified durations such as in a range between about 2 hours and about 12 hours, or in a range between about 4 hours and about 10 hours, or in a range between about 6 hours and about 8 hours, or any time point between any of these ranges. Typically, the voltage 28 is supplied overnight, or while the subject 12 is sleeping/resting so as to mimic the circadian rhythm of natural testosterone production. Thus, in some embodiments, the voltage 28 is supplied for a duration of about 6 hours or about 8 hours. The optional timer 38 may also allow the voltage 28 to be supplied in pulses wherein for each pulse the voltage 28 is supplied for a period of time that alternates with a period of time during which no voltage is supplied.

The voltage 28 may also be supplied in a constant setting such that a constant voltage is delivered, or may be delivered in such a way that the voltage supplied alternates between a first voltage and a second voltage wherein the first voltage is different from the second voltage. The first voltage may be greater than the second voltage or the first voltage may be less than the first voltage. The voltage may also be supplied such that the voltage gradually increases and decreases or the voltage differences may increase and decrease in steps.

The voltage 28 may also be supplied such that it cycles between the first and second electrodes 14, 18. For example, the voltage 28 may be supplied in the form of alternating current. Or devices having a direct current power source 22, could include a switching feature that alternately applies the voltage 28 to the first and second electrodes 14, 18.

While embodiments of the device 10 and method have been described as having a first electrode 14 and a second electrode 18, it is understood that the device 10 and methods could employ additional electrodes, such as a third 70 or fourth electrode that in contact with the skin in the pubic region 16 or the scrotum 20 of the subject 12.

EXAMPLE

The subject was diagnosed as having a low testosterone blood level after the subject's blood level of testosterone, sex hormone binding globulin, and albumin were measured as follows: total testosterone 310 ng/dl, free testosterone 35.3 ng/dl, bioavailable testosterone 77.2 ng/dl, sex hormone binding globulin 37 nmol/dl, and albumin 4.8 g/dl.

After a round of Androgel® treatment at a dose of 5 g applied daily for a period of 48 days, the subject's blood level of testosterone, sex hormone binding globulin, and albumin were measured as follows: total testosterone 544 ng/dl, free testosterone 115 ng/dl, bioavailable testosterone 217.7 ng/dl, sex hormone binding globulin 44 nmol/dl, and albumin 4.1 g/dl.

While continuing the Androgel® treatment, the subject developed and started using embodiments of the invention to stimulate the endogenous production of testosterone from his testicles. The subject applied a voltage of 3 volts to his testicles and pubic region while he slept for approximately 6 hours to 8 hours a night. The voltage was supplied to the testicles by two electrodes with the first electrode placed in his pubic region about 1 to 3 inches from the base of his penis and the second electrode placed on his scrotum. The subject shaved the skin in the area where the electrodes were placed. The electrodes were 1.75" diameter carbon graphite electrodes that were coated with a conductive gel before each use. The electrodes were held in place by a tight fitting undergarment that had a hole in the front so that the penis could pass through. The voltage was constantly supplied by a 3 volt DC battery (1 mAmps) every night. The subject measured the voltage of 30 mV passing through the skin with a voltmeter with the voltmeters contacts placed in the area between the two electrodes. After approximately 60 days of using the device, the subject's blood level of testosterone, sex hormone binding globulin, and albumin were measured as follows: total testosterone 1090 ng/dl, free testosterone 204.3 ng/dl, bioavailable testosterone 420.2 ng/dl, sex hormone binding globulin 28 nmol/dl, and albumin 4.5 g/dl.

After some experimentation, the subject observed that low voltage, i.e., less than 6 volts, may be applied overnight with minimal discomfort, whereas voltages greater than about 6 volts caused either immediate discomfort and/or burns.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative example shown and described. Accordingly, departures may be made from such details without departing from the scope or spirit of the general inventive concept.

What is claimed is:

1. A method of stimulating testosterone production in a male subject comprising:
   contacting the skin in the pubic region of the subject with a first electrode;
   contacting the skin of the scrotum of the subject with a second electrode, wherein the first electrode and the second electrode are coupled to a power source;
   supplying a voltage from the power source to one of the first electrode or the second electrode, wherein at least a portion of the voltage passes through the skin of the subject from the first or second electrode that is supplied with the voltage to the other of the first or second electrode to complete the circuit with the power source, wherein the voltage supplied from the first or second electrode is about 6 volts or less and is sufficient to stimulate testosterone production in the subject.

2. The method of claim 1 wherein the voltage supplied is about 3 volts or less.

3. The method of claim 1 wherein the voltage is supplied for about 2 hours to about 12 hours in a 24 hour period.

4. The method of claim 1 wherein the voltage is supplied for about 4 hours to about 8 hours.

5. The method of claim 1 wherein the voltage is supplied while the subject is sleeping.

6. The method of claim 1 wherein the voltage is supplied in repeated on/off pulses.

7. The method of claim 1 wherein the voltage of the voltage supplied alternates between a first voltage and a second voltage wherein the first voltage is greater than the second voltage.

\* \* \* \* \*